(12) United States Patent
Armbruster

(10) Patent No.: US 11,751,775 B2
(45) Date of Patent: Sep. 12, 2023

(54) ELECTRICAL DEVICE FOR MONITORING, PREVENTION, AND TREATMENT OF IMPLANT INFECTIONS

(71) Applicant: DePuy Synthes Products, Inc., Raynham, MA (US)

(72) Inventor: David Armbruster, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 309 days.

(21) Appl. No.: 16/999,597

(22) Filed: Aug. 21, 2020

(65) Prior Publication Data

US 2021/0059554 A1 Mar. 4, 2021

Related U.S. Application Data

(60) Provisional application No. 62/894,311, filed on Aug. 30, 2019.

(51) Int. Cl.
*A61B 5/053* (2021.01)
*G16H 50/20* (2018.01)
(Continued)

(52) U.S. Cl.
CPC ............ *A61B 5/053* (2013.01); *A61B 5/0002* (2013.01); *A61B 5/746* (2013.01); *A61B 17/64* (2013.01); *G16H 50/20* (2018.01)

(58) Field of Classification Search
CPC ....... A61B 5/053; A61B 5/0002; A61B 5/746; A61B 17/64; A61B 5/0538;
(Continued)

(56) References Cited

U.S. PATENT DOCUMENTS 4,549,547 A 10/1985 Brighton et al.
4,993,413 A 2/1991 McLeod et al.
(Continued)

FOREIGN PATENT DOCUMENTS

EP 2384168 A1 11/2011
WO 2016/113440 A1 7/2016

OTHER PUBLICATIONS

Arnout J. van der Borden et al., Prevention of pin tract infection in external stainless steel fixator frames using electric current in a goat model, Biomaterials, 28, 2122-2126, 2007 (Year: 2007).*
(Continued)

*Primary Examiner* — Eric F Winakur
*Assistant Examiner* — Jonathan Drew Moroneso
(74) *Attorney, Agent, or Firm* — Dunlap Codding, P.C.

(57) ABSTRACT

A device, having a housing; a power source configured to supply electrical power to a conductive percutaneous implant in a circuit including the conductive percutaneous implant and tissue of a patient adjacent to the conductive percutaneous implant; an electrical sensor configured to generate a signal indicative of at least one electrical parameter of the circuit; and at least one data processing system having one or more processors configured to receive the signal and analyze the signal to determine at least one of a presence or change of infection of the tissue, and pass a control signal to the power source to vary the electrical power responsive to determining at least one of the presence or change of infection of the tissue.

20 Claims, 9 Drawing Sheets

(51) Int. Cl.
*A61B 5/00* (2006.01)
*A61B 17/64* (2006.01)

(58) Field of Classification Search
CPC .......... A61B 2560/0219; A61B 5/6801; A61B 5/7264; A61B 5/4842; G16H 50/20; G16H 40/63; A61N 1/0502; A61N 1/205; A61N 1/326; A61N 1/36017; A61N 1/36031; A61N 1/0468; A61N 1/0484
See application file for complete search history.

(56) References Cited

U.S. PATENT DOCUMENTS

| | | | |
|---|---|---|---|
| 6,146,586 | A | 11/2000 | McLeod et al. |
| 7,756,586 | B2 | 7/2010 | Wenzel et al. |
| 8,135,466 | B2 | 3/2012 | Wysk et al. |
| 8,663,914 | B2 | 3/2014 | Ren et al. |
| 8,900,217 | B2 | 12/2014 | Malhi |
| 9,174,042 | B2 | 11/2015 | Schonenberger et al. |
| 9,320,832 | B2 | 4/2016 | Joseph et al. |
| 9,592,160 | B2 | 3/2017 | Bacon et al. |
| 9,616,142 | B2 | 4/2017 | Ehrensberger et al. |
| 10,000,491 | B2 | 6/2018 | Rogachefsky et al. |
| 10,226,214 | B2 | 3/2019 | Ogrondnik et al. |
| 2008/0064980 | A1 | 3/2008 | Lee et al. |
| 2010/0204802 | A1 | 8/2010 | Wilson et al. |
| 2015/0073491 | A1* | 3/2015 | Ehrensberger ............ A61L 2/24 607/116 |
| 2017/0000918 | A1 | 1/2017 | Ehrensberger et al. |
| 2017/0056536 | A1 | 3/2017 | Hallab et al. |
| 2018/0220947 | A1* | 8/2018 | Bedell, Jr. .......... A61B 5/02416 |
| 2018/0369582 | A9 | 12/2018 | Bogie et al. |
| 2020/0178906 | A1* | 6/2020 | Bevan ................ A61B 5/02055 |
| 2022/0117511 | A1* | 4/2022 | Shor .................... A61B 5/0538 |

OTHER PUBLICATIONS

Isaacson, et al.; "Bioelectric Analyses of an Osseointegrated Intelligent Implant Design System".; Journal of Visualized Experiments, (2009), vol. 29, e1237, pp. 1-5.

Maathuis, P.G.M.; "Detection, Prevention and Direct Post-Operative Intervention in Orthopaedic Implant Infection" (2007); University of Groningen/UMCG research database.

Niepa et al.; "Eradication of Pseudomonas Aeruginosa Cells by Cathodic Electrochemical Currents Delivered with Graphite Electrodes". Acta Biomater (2017), http://dxdoi/otg/10/1016/jactbio.2016.12.053.

Nodzo et al.; "Cathodic Voltage-controlled Electrical Stimulation Plus Prolonged Vancomycin Reduce Bacterial Burden of a Titanium Implant-associated Infection in a Rodent Model." Clinical Orthopaedics and Related Research (2016), vol. 474, No. 7, pp. 1668-1675.

Van Der Borden et al.; "Prevention of Pin Tract Infection in External Stainless Steel Fixator Frames Using Electric Current in a Goat Model." Biomaterials (2007) vol. 28, pp. 2122-2126.

International Preliminary Report on Patentability and Written Opinion of the International Searching Authority, dated Jan. 3, 2022, in PCT/IB2020/057860, filed Aug. 21, 2020.

Aktuglu, et al.; "Ilizarov Bone Transport and Treatment of Critical-Sized Tibial Bone Defects: A Narrative Review," Journal of Orthopaedics and Traumatology (2019), vol. 20, No. 22, pp. 1-14.

Brånemark, et al.; "Osseointegrated Percutaneous Prosthetic System for the Treatment of Patients With Transfemoral Amputation: A Prospective Five-year Follow-up of Patient-reported Outcomes and Complications," Journal of the American Academy of Orthopaedic Surgeons (2019), vol. 27, No. 16, pp. e743-e751.

Ferreira, et al.; "Prevention and Managment of External Fixator Pin Track Sepsis," Strat Tram Lim Recon (2012), vol. 7. pp. 67-72.

* cited by examiner

ELECTRICAL DEVICE FOR MONITORING, PREVENTION, AND TREATMENT OF IMPLANT INFECTIONS

CROSS REFERENCE TO RELATED APPLICATIONS

The present application claims priority under 35 U.S.C. § 119€ to U.S. Ser. No. 62/894,311, filed Aug. 30, 2019, the entirety of which is hereby expressly incorporated by reference herein.

BACKGROUND

Implant infections—for example, but not by way of limitation, pin tract infections—are very common complications associated with surgical procedures where at least a portion of an implant extends outwardly from the tissue and beyond the surface of the skin and, with respect to pin tract infections in particular, orthopaedic external fixation implants such as pins. Bacteria can contaminate the skin surrounding the implants and the surface of the implants and cause soft tissue infection, which can progress to deeper bone infection or osteomyelitis. Soft tissue infection can often be treated effectively with oral antibiotics and local skin treatment; however, deeper bone infection typically requires removal of percutaneous implants or abandonment of external fixation altogether, in one example. Implant infections often cannot be treated by systemic or oral antibiotics, because the bacteria form a biofilm on the metal surface of the implant. In a biofilm, bacteria secrete an extracellular slime layer and reduce their metabolic activity to become resistant to the host immune system and systemic antibiotics. Currently, clinicians recommend a variety of techniques to try to prevent implant infections, including local antiseptics and regular implant site cleaning. Despite aggressive treatments, however, implant infections, such as pin tract infections in particular, are the most common complication of external fixation, with a quoted incidence ranging from 11.3% to 100% (Ferreira and Marais, "Prevention and management of external fixator pin tract sepsis." *Strat Traum Limb Recon*, 2012 7:67-72; Aktuglu et al., "Ilizarov bone transport and treatment of critical-sized tibial bone defects: a narrative review." *J Orthop Traumatol*. 2019 Apr. 16; 20(1):22). In addition, the risk of implant infections increases with time; for example, the longer an external fixation implant such as a pin remains in place, the higher the risk of infection and the more severe the infection becomes. With more recently developed surgical treatments such as distraction osteogenesis, external fixation implants can remain in place for many months. The success of these distraction osteogenesis procedures depends upon the ability to maintain the fixation implants infection-free for long periods.

Implant site infections of pins associated with external fixators in reconstructive bone surgery frequently occur and constitute a major concern for orthopaedic surgeons. Prevention of these types of implant site infections is also an important nursing responsibility, but there is no consensus on how to perform optimal implant site care (Ferreira and Marais (2012)). When an implant site becomes infected, it is usually difficult to treat due to the formation of biofilm around the metal surface. The biofilm mode of growth shields the bacteria from the host defence mechanism and antibiotics. Literature indicates that 500-5000 times higher levels of antibiotics are needed to achieve the same antimicrobial effects on biofilm bacteria than needed for planktonic bacteria.

Percutaneous osseointegrated prostheses (POP) are bone implants utilized following the amputation of a portion of a long bone such as the femur or humerus, to provide for direct connection of a limb prosthesis to the skeleton. POP implants provide improved function and comfort relative to traditional prostheses, however infection at the skin-implant interface is common, with over 25% of patients experiencing deep tissue infections in some published clinical series [Brånemark, R P, Hagberg, K, Kulbacka-Ortiz, MS, Berlin, Ö, Rydevik, B (2018) Osseointegrated Percutaneous Prosthetic System for the Treatment of Patients With Transfemoral Amputation: A Prospective Five-year Follow-up of Patient-reported Outcomes and Complications. J Am Acad Orthop Surg; December 13:1-9]. Treatment of implant related infection of POP implants can be complicated due to the biofilm nature of the infection, which makes systemic antibiotics often ineffective.

The development of a biomaterials-associated infection starts with the adhesion of bacteria to the biomaterials surface, as mediated by attractive Lifshitz-Van der Waals forces, acid-base interactions, and electrostatic forces. Because all naturally occurring surfaces, including those of bacterial cells, are generally negatively charged, the electrostatic force between bacteria and a biomaterials surface is repulsive. These repulsive forces can be enhanced by application of an electric current, thereby increasing the negative charge and consequently the repulsive force.

It has been demonstrated that it is possible to detach more than 60-76% of staphylococci adhering to surgical stainless steel surfaces through the application of small electric currents (100 mA or less); it has also been demonstrated that staphylococci growing in a biofilm could be detached through the application of an electric current, most notably in the absence of any biocide. An electric current has been known before to enhance the bactericidal effects of many biocides, an effect called the "bioelectric effect," whereas a direct bactericidal effect of electric currents has also been described. Recently, this direct bactericidal effect has been observed on bacteria that remained adhering after electric current induced detachment in the absence of any antibiotics. (van der Borden, et al., "Prevention of pin tract infection in external stainless-steel fixator frames using electric current in a goat model." *Biomaterials*, (2007) 28(12), 2122-2126).

It has been observed, for example, that application of 100 microamperes current to an external fixator reduces the likelihood of an infection developing in the tissue surrounding the external fixator. It has also been observed that the development and worsening of an infection in the tissue surrounding the external fixator decreases electrical resistance in the tissue surrounding the external fixator (van der Borden et al. (2007) *Biomaterials*, 28(12):2122-2126).

The prior art, however, does not provide an electrical device that is suitable for widespread use to prevent or treat an infection developing in the tissue surrounding an implant—such as a pin in conjunction with an external fixator. It is to such an improved electrical device and methods for its use that the present disclosure is directed.

BRIEF DESCRIPTION OF THE DRAWINGS

These and other objects and features of the present inventive concepts will be more fully disclosed or rendered obvious by the following detailed description, which is to be considered together with the accompanying drawings wherein like numbers refer to like parts, and further wherein.

DETAILED DESCRIPTION OF EXEMPLARY EMBODIMENTS

Figure 1:
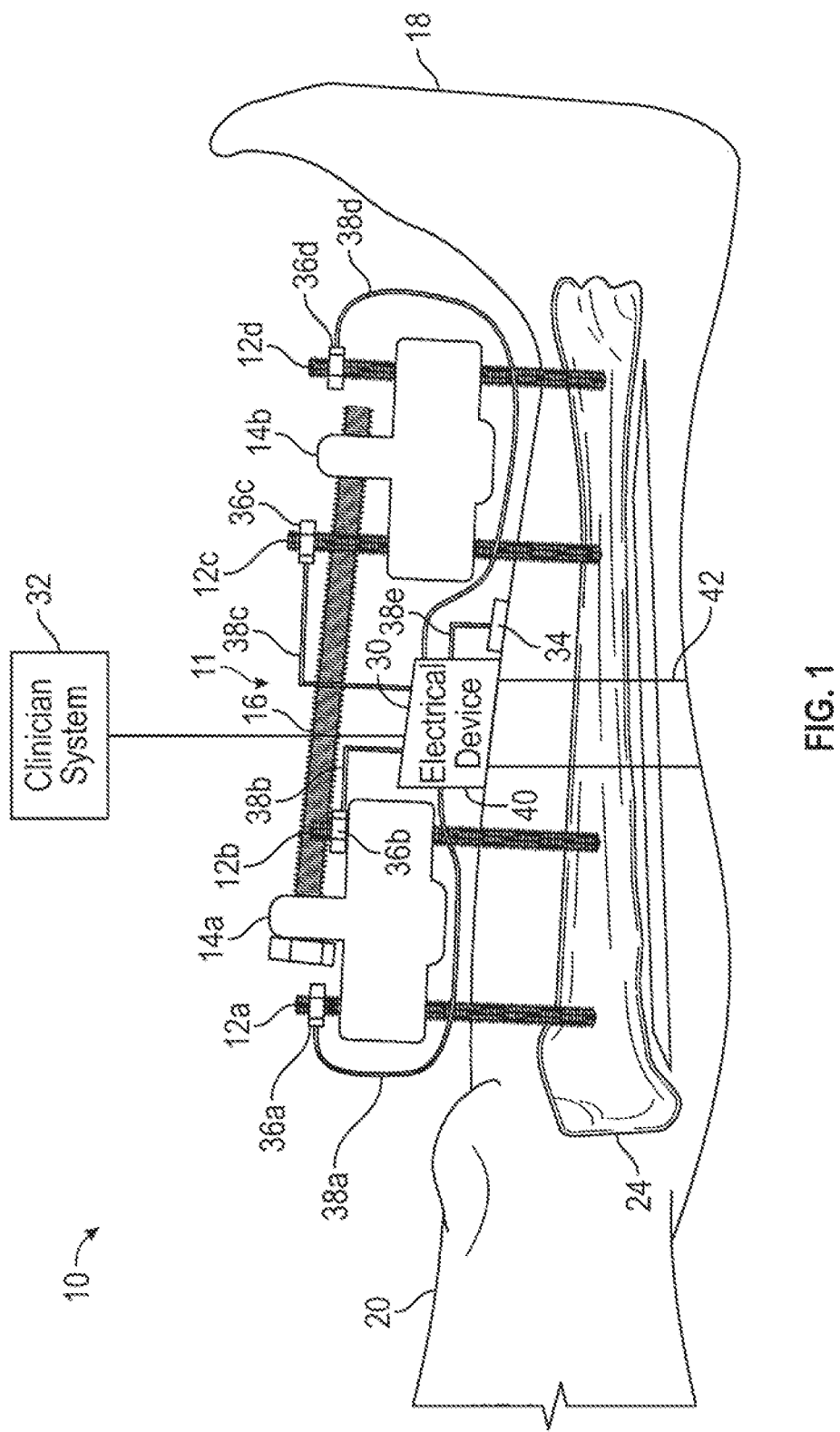
FIG. 1 is a diagrammatic view of an external fixation system having an electrical device constructed in accordance with the present disclosure mounted to a leg of a patient having four conductive percutaneous implants passing through skin and fixated to a bone within the patient.

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, certain well-known features may not be described in detail in order to avoid unnecessarily complicating the instant disclosure.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the medical procedures and techniques of, surgery, anesthesia, wound healing, and infection control described herein are those well-known and commonly used in the art. Standard techniques are used for infection diagnostic and therapeutic applications.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles, compositions, kits, and/or methods disclosed herein can be made and executed without undue experimentation in light of the present disclosure. While the articles, compositions, kits, and/or methods have been described in terms of particular embodiments, it will be apparent to those of skill in the art that variations may be applied to the articles, compositions, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

The use of ordinal number terminology (i.e., "first," "second," "third," "fourth," etc.) is solely for the purpose of differentiating between two or more items and, unless explicitly stated otherwise, is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B is true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps. For example, a process, method, article, or apparatus that comprises a list of elements is not necessarily limited to only those elements but may include other elements not expressly listed or inherently present therein.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

As used herein, the term "patient" or "subject" is meant to include all organisms, whether alive or dead, including any species having soft tissues and bones. For example, a method according to the inventive concepts disclosed herein may be used for infection control for a living human, horse, cow, sheep, cat, dog, and the like.

As used herein, the term "implant" refers to a device that is inserted or fixed in living tissue within a patient's body, especially by surgery. More particularly, the implant is a percutaneous device inserted through the skin and extending away from the implant site and at a distance above the outer surface of the patient's skin. Exemplary implants include a pin, or a prosthetic device. An exemplary prosthetic device is a percutaneous osseointegrated prosthesis for amputees.

Certain non-limiting embodiments of the present disclosure are directed to a device that includes: a housing which may be configured to be worn by a patient, a power source, an electrical sensor, and at least one data processing system. The power source is configured to supply electrical power to a conductive percutaneous implant in a circuit including the conductive percutaneous implant and a tissue adjacent to the conductive percutaneous implant. The electrical sensor is configured to generate a signal indicative of at least one electrical parameter of the circuit. In addition, the at least one data processing system has one or more processors configured to receive the signal and analyze the signal to determine at least one of a presence or change of infection of the tissue, and pass a control signal to the power source to vary the electrical power responsive to determining at least one of the presence or change of infection of the tissue. In certain non-limiting embodiments, the conductive percutaneous implant includes a pin or percutaneous osseointegrated prosthesis for amputees, for example. Additionally, in these non-limiting embodiments and/or other exemplary non-limiting embodiments the conductive percutaneous implant extends away from the implant site and at a distance above the outer surface of the patient's skin.

In certain non-limiting embodiments, the housing of the device has a band configured to be worn by the patient.

In certain non-limiting embodiments, the electrical sensor monitors resistance within the circuit.

In certain non-limiting embodiments, the power source includes a reference electrode configured to be placed upon a skin of the patient.

In certain non-limiting embodiments, the power source is connected to an implant connector sized and dimensioned to be connected to the conductive percutaneous implant, while the implant connector has a body, a first electrode, and a second electrode. The body supports the first electrode and the second electrode. The first electrode is positioned to engage the first conductive percutaneous implant, and the second electrode is positioned to engage a skin of the patient. The body electrically isolates the first electrode from the second electrode.

In certain non-limiting embodiments, the power source includes a reference electrode configured to be within the circuit, and the reference electrode has an implant connector configured to be connected to a third conductive percutaneous implant.

In certain non-limiting embodiments, the device further comprises a wireless communication device, and the one or more processors is configured to provide an alert to the wireless communication device and enable the wireless communication device to transmit the alert based upon the signal.

In certain non-limiting embodiments, the signal is analyzed by supplying the signal to an artificial intelligence network trained with a percutaneous implant data model to determine at least one of the presence or change of infection of the tissue.

In certain non-limiting embodiments, the signal is analyzed by comparing the respective signal to a stored infection parameter to determine at least one of the presence or change of infection of the tissue.

In certain non-limiting embodiments, the electrical power is varied by increasing an amount of the electrical power.

Certain non-limiting embodiments of the present disclosure are directed to a non-transitory computer readable medium storing computer executable instructions that when executed by one or more processor cause the one or more processor to: receive information correlating a first lead of a power supply to a first conductive percutaneous implant, a second lead of the power supply to a second conductive percutaneous implant, and a third lead of the power supply to a third conductive percutaneous implant, the power supply being a potentiostat; monitor a first circuit including the first lead and the first conductive percutaneous implant for at least one electrical parameter indicative of an infection present adjacent to the first conductive percutaneous implant; designate the first lead as a working electrode, the second lead as a reference electrode, and the third lead as a counter electrode; and pass a control signal to the power supply with instructions to supply electrical current through the working and counter electrodes such that a first electrical potential of the working electrode is substantially constant relative to a second electrical potential of the reference electrode.

Certain non-limiting embodiments of the present disclosure are directed to a wearable device that includes: a housing configured to be worn by a patient; a first power source; an electrical sensor; and at least one data processing system. The power source is configured to supply electrical power to a conductive percutaneous implant in a circuit including the conductive percutaneous implant and a tissue adjacent to the conductive percutaneous implant. The electrical sensor is configured to generate a signal indicative of at least one electrical parameter of the circuit. The at least one data processing system has one or more processors configured to receive the signal and analyze the signal to determine an infection status of the, the infection status being infected or not infected, and pass a control signal to the power source to vary the electrical power responsive to the infection status of the tissue being infected.

In certain non-limiting embodiments, the housing has a band configured to be worn by the patient.

In certain non-limiting embodiments, the electrical sensor monitors resistance within the circuit.

In certain non-limiting embodiments, the power source includes a reference electrode configured to be placed upon a skin of the patient.

In certain non-limiting embodiments, the power source is connected to an implant connector sized and dimensioned to be connected to the conductive percutaneous implant. The implant connector has a body, a first electrode, and a second electrode. The body supports the first electrode and the second electrode. The first electrode is positioned to engage the first conductive percutaneous implant, and the second electrode is positioned to engage the skin of the patient. The body electrically isolates the first electrode from the second electrode.

In certain non-limiting embodiments, the power source includes a reference electrode configured to be within the circuit. The reference electrode has an implant connector configured to be connected to a third conductive percutaneous implant.

In certain non-limiting embodiments, the device further comprises a wireless communication device, and the one or more processors is configured to provide an alert to the wireless communication device and enable the wireless communication device to transmit the alert responsive to the infection status of the tissue being infected.

In certain non-limiting embodiments, the signal is analyzed by supplying the signal to an artificial intelligence network trained with a percutaneous implant data model to determine the infection status of the tissue.

In certain non-limiting embodiments, the signal is analyzed by comparing the signal to a stored infection parameter to determine the infection status of the tissue.

In certain non-limiting embodiments, the electrical power is varied by increasing an amount of the electrical power.

Certain non-limiting embodiments of the present disclosure are directed to a method, comprising: forming an electrical circuit at a percutaneous implant passing through skin and fixated within a body, the electrical circuit including a power source, the conductive percutaneous implant, and tissue surrounding the conductive percutaneous implant; monitoring at least one electrical parameter in the electrical circuit; determining a presence of an infection due to the electrical parameter; and varying electrical power within the electrical circuit responsive to determining the presence of the infection.

Certain exemplary embodiments of the present disclosure will now be described with reference to the drawings.

Referring now to the Figures, and in particular to FIG. 1, illustrated therein is an external fixation system 10 constructed in accordance with the present disclosure. In general, the external fixation system 10 is provided with an adjustable fixator 11, including a plurality of percutaneous implants 12, two implant clamps 14, and a connecting rod 16 connecting the implant clamps 14. The connecting rod 16 can be a carbon fiber rod, for example but not by way of limitation. By way of example, four percutaneous implants 12 are shown in FIG. 1 and designated with the reference numerals 12a, 12b, 12c and 12d. It should be understood, however, that the adjustable fixator 11 can have more or less of the percutaneous implants 12. The percutaneous implants 12 are constructed of a biocompatible and conductive material such as (but not limited to) stainless steel, titanium or titanium alloys. For purposes of clarity, the implant clamps are designated with reference numerals 14a and 14b. The implant clamp 14a is connected to the percutaneous implants 12a and 12b. The implant clamp 14b is connected to the percutaneous implants 12c and 12d. The distance between the implant clamps 14a and 14b can be adjusted by moving the position of attachment of clamps 14a and 14b to the connecting rod 16.

In use, the percutaneous implants 12 are fixed within a patient 18. In the example shown, the percutaneous implants 12 extend through skin 20 and tissue of the patient 18 and into a bone 24 of the patient 18. In this example, the bone 24 is a tibia. It should be understood, however, that the bone 24 could be other bones within the patient 18, such as (but not limited to) the femur, radius, humerus, or a bone associated with the pelvis, arm, or wrist of the patient 18. Although this example shows all four of the percutaneous implants 12 being positioned within a single bone 24, it should be understood that the percutaneous implants 12 may be positioned in separate bones. For example, the adjustable fixator 11 may be a modular knee bridge in which two or more of the percutaneous implants 12 are positioned within a femur, while two or more of the percutaneous implants 12 are positioned within a tibia of the patient 18.

The external fixation system 10 is also provided with an electrical device 30 and a clinician system 32 in accordance with the present disclosure. The electrical device 30 can be configured to be worn by the patient 18. In some embodiments, the electrical device 30 may not be configured to be worn by the patient 18. Generally, the electrical device 30 may provide electrical energy to the percutaneous implants 12 when the adjustable fixator 11 is installed on the patient 18 to prevent or treat infections such as the type of infections arising along pin tracts. In some non-limiting embodiments, the electrical device 30 measures an electrical parameter associated with each of the percutaneous implants 12 so as to determine an infection status for each percutaneous implant 12. Based upon the infection status of each percutaneous implant 12, the electrical device 30 can vary (for each percutaneous implant 12 or group of percutaneous implants 12) at least one property of the electrical energy supplied to the percutaneous implants 12. The at least one property may be (a) a type of electrical energy such as (but not limited to) DC or AC, (b) a voltage of the electrical energy (constant or variable), (c) a current of the electrical energy (constant or variable), (d) a schedule for application/removal of the electrical energy, (e) a shape of the waveform (including pulse width) of the electrical energy, (f) combinations of any of the above, or the like. When the infection status of any of the percutaneous implants 12 changes, an alert can be passed from the electrical device 30 to the clinician system 32. The clinician system 32 can be a computer associated with a particular clinic or clinician. For example, the clinician system 32 can be a personal computer, a tablet computer, a smart phone, a smart watch, and combinations thereof. In any event, communication between the electrical device 30 and the clinician system 32 can be accomplished by connecting the electrical device 30 to a network, for example. The network can be a local area network, a wide area network, or combinations thereof.

The alert can notify the patient's clinician of the infection status at various intervals and/or at various times. In some non-limiting embodiments, the electrical device 30 is configured to communicate bi-directionally with the clinician system 32. In these embodiments, the clinician can use the remotely reported data to make or modify at least one treatment plan for the patient 18. The electrical device 30 can be: (1) used prophylactically to prevent percutaneous implant 12 infections, (2) used to treat an infection by changing the property of electrical energy supplied to a particular percutaneous implant 12 by the electrical device 30, or (3) applied to the percutaneous implants 12 after an infection has been diagnosed without the aid of the electrical device 30.

In some non-limiting embodiments, the electrical device 30 includes a reference electrode 34 and a plurality of implant connectors 36. In some non-limiting embodiments, such as (but not limited to) the embodiment of FIG. 5, one of the percutaneous implants 12 can be used as the reference electrode 34. In the embodiment of FIG. 1, the reference electrode 34 is applied to the skin 20 of the patient 18. It should be understood, however, that the reference electrode 34 can be a needle or percutaneous wire extending through the skin 20. As shown in FIG. 1, the reference electrode 34 can be placed between at least two adjacently disposed percutaneous implants 12, such as (but not limited to) the percutaneous implants 12b and 12c. The preferred location of the reference electrode 34 is near the percutaneous implants 12a, 12b, and 12c, but spaced a sufficient distance away so as to be unaffected by local electrical currents around the percutaneous implants 12a, 12b, and 12c.

In the example shown, the electrical device 30 includes four implant connectors that are designated in FIG. 1 with the reference numerals 36a, 36b, 36c, and 36d. The implant connector 36a is connected to the percutaneous implant 12a; the implant connector 36b is connected to the percutaneous implant 12b; the implant connector 36c is connected to the percutaneous implant 12c; and the implant connector 36d is connected to the percutaneous implant 12d. The implant connectors 36 are constructed of a conductive material such as (but not limited to) stainless steel, titanium, copper, or the like that is compatible with the percutaneous implants 12 so as to prevent the formation of galvanic corrosion between the implant connectors 36 and the percutaneous implants 12. Depending upon the type of procedure for which the adjustable fixator 11 is being used, it is possible that the implant connectors 36 will be applied to the percutaneous implants 12 for a significant period of time, such as (but not limited to) weeks or months. For this reason, it is preferred that the implant connectors 36 be constructed in a rugged and reliable manner so as to maintain an electrical connection between the implant connectors 36 and the percutaneous implants 12. The implant connectors 36 may be constructed in any suitable manner, such as (but not limited to) a clamp or a clip. The electrical device 30 is also provided with a plurality of leads 38 (labelled in FIG. 1 as 38a-d) so as to connect circuitry of the electrical device 30 to the implant connectors 36 and the reference electrode 34 and thereby supply electrical energy to the percutaneous implants 12 and/or monitor the at least one electrical parameter. The leads 38a-e are constructed of at least one conductive material, such as (but not limited to) gold, silver, copper, or aluminum.

The electrical device 30 may also be provided with a housing 40 configured to be worn by the patient 18. The housing 40 may include (or be attached to) a strap 42 for securing the electrical device 30 onto the patient 18. The electrical device 30 can also be provided in the form of an anklet, bracelet, or ring, depending upon the location on the body of the patient 18 where the electrical device 30 will be worn. The electrical device 30 could also be worn on a belt, carried in a shoulder bag such as a purse or backpack, or otherwise fashioned so as to be carried on or by the patient 19. The housing 40 of the electrical device 30 may be formed of any material configured to be worn on the patient 18. In some non-limiting embodiments, the housing 40 may be formed of a waterproof material for protecting one or more components housed within the electrical device 30. The housing 40 may be formed in any shape including, but not limited to, a sphere, a ring, a cone, a cube, a rectangular prism, a cylinder, a triangular prism, a pyramid, and/or any fanciful shape. In the example depicted in FIG. 1, the housing 40 is formed into a shape of a rectangular prism. The housing 40 may include an arc-shaped portion to mate against the patient 18.

Figure 2:
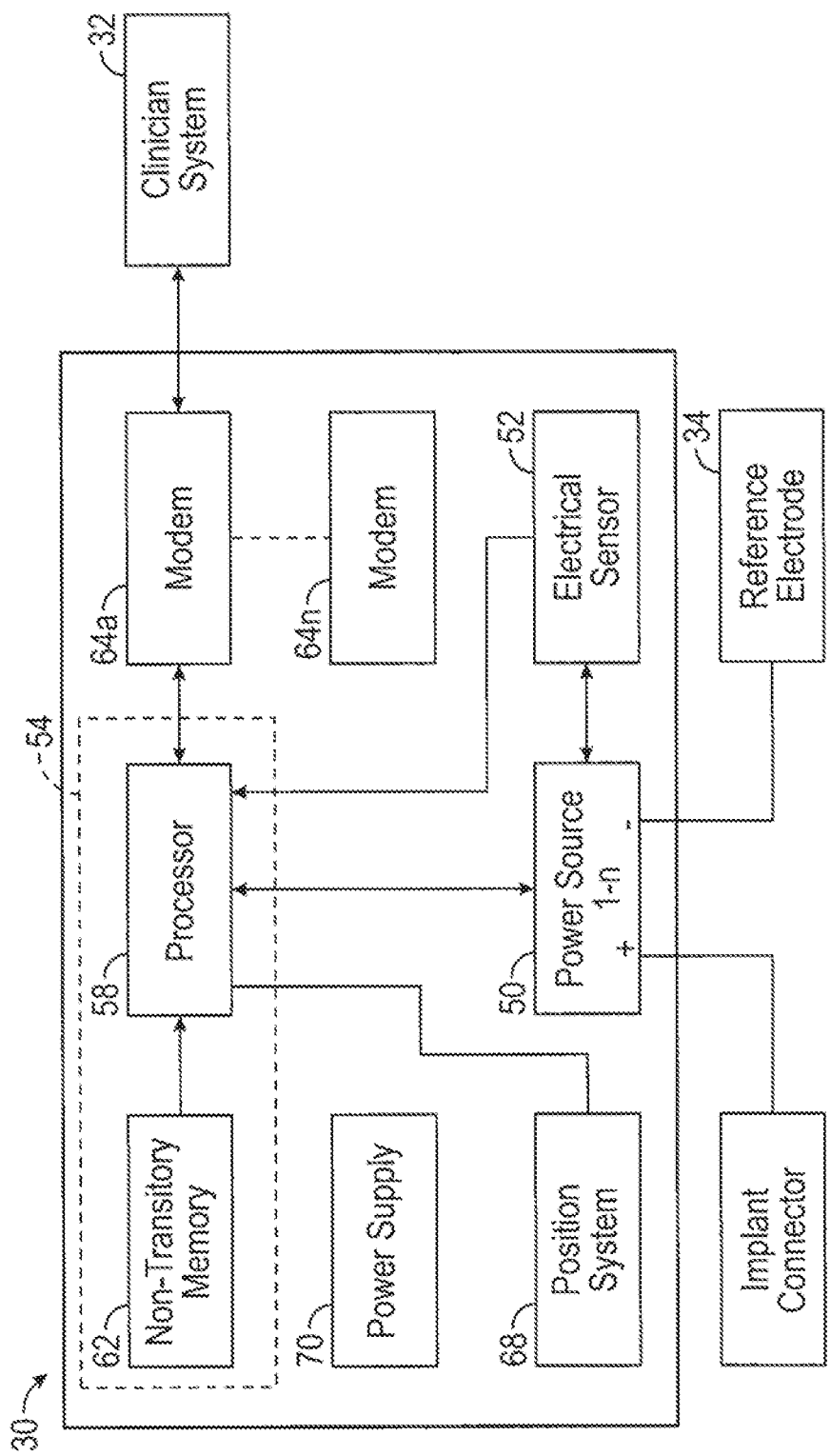
FIG. 2 is a block diagram of an exemplary electrical device illustrated in FIG. 1.

Referring now to FIG. 2 in combination with FIG. 1, shown therein is an embodiment of the electrical device 30 constructed in accordance with the present disclosure. In general, the electrical device 30 may be provided with at least one power source 50, at least one electrical sensor 52 for each power source 50, and at least one data processing system 54. Each of the power sources 50 is configured to supply electrical power to at least one of the percutaneous implants 12 in a circuit including the percutaneous implant 12, tissue of the patient 18 adjacent to the percutaneous implant 12, and the reference electrode 34. The at least one electrical sensor 52 is configured to generate a signal indicative of at least one electrical parameter of the circuit.

The electrical parameter can be current, voltage, conductivity, or resistance. The electrical sensor 52 can be a voltmeter, an ohm meter, or an ammeter. In some non-limiting embodiments, the electrical device 30 has the ability to measure the conductivity (and resistance) of the soft tissue around each of the percutaneous implants 12, i.e., in this example, between one of the percutaneous implants 12 and the reference electrode 34. Soft-tissue conductivity will change based on local infection status due to the increased water content of infected tissue and thus may be used to diagnose infection.

The at least one data processing system 54 has one or more processors 58 configured to receive the signal from the electrical sensor(s) 52 and analyse the signal to determine an infection status of at least one of the percutaneous implants 12. The infection status is an indication of the presence or change of infection of the tissue within the circuit. The processor 58 can be programmed with a unique identifier for each of the percutaneous implants 12 so that the infection status for each percutaneous implant 12 can be logged at distinct instances of time, updated in batch form or at distinct instances of time, and/or tracked during a period of time.

In the example shown in FIG. 1, the wearable electric device 30 is provided with four power sources 50 (i.e., one power source 50 for each of the percutaneous implants 12) and four electrical sensors 52, and four separate circuits are formed (i.e., one circuit for each of the percutaneous implants 12). In this example, the processor 58 of the data processing system 54 may be configured to periodically analyse and determine an infection status for each of the percutaneous implants 12. Infection status for each of the percutaneous implants 12 can be stored in a non-transitory computer readable medium 62 coupled with the processor 58 and associated with a particular one of the percutaneous implants 12. When the processor 58 determines a presence or change of infection of the tissue with respect to a particular percutaneous implant 12, the processor 58 may pass a control signal to the power source 50 to vary the electrical power supplied to the particular percutaneous implant 12. For example, when the processor 58 determines that an infection exists within the tissue, the processor 58 may output a control signal to increase the electrical power, e.g., voltage and/or the current, supplied to the particular percutaneous implant 12. When the processor 58 determines that an infection does not exist within the tissue, the processor 58 may output a control signal reducing the voltage and/or the current supplied to the particular percutaneous implant 12. This process can be repeated continuously (or intermittently) to measure and treat infection individually for each of the percutaneous implants 12.

The electrical device 30 may also be provided with one or more wireless communication devices (i.e., modem 64) for communicating data and/or receiving instructions to form a treatment plan from the clinician system 32. Multiple types of modems 64a-n can be provided so as to provide flexibility with the implementation of the electrical device 30. For example, the modems 64a-n may conform to the requirements of various versions or families of IEEE 802.11 in various frequencies including but not limited to 2.4 GHz, 5 GHz, and 60 GHz frequency bands so as to be able to communicate with many commercially available types of local area networks. These local area networks can be coupled to a wide area network, such as (but not limited to) the Internet, to permit communication between the electrical device 30 and the clinician's system 32. One or more of the modems 64a-n may also conform to the requirements of cellular data transmission so as to able to communicate by way of a cellular telephone network.

The electrical device 30 may also be provided with one or more position system 68, such as (but not limited to) an inertial measurement unit (IMU) having gyroscopes, accelerometers, and/or magnetometers for determining position data including but not limited to the orientation and/or movement of the electrical device 30 at particular instances of time. The position data can be supplied to the processor 58 and used to determine whether the patient 18 is moving or at rest. If the patient 18 is moving, the position data can be used to determine the type of movement, i.e., walking movement, swinging movement (due to the use of crutches), or smooth rolling movement (due to the use of a wheelchair). When the patient 18 is at rest, an orientation of the bone 24 can be determined. This information may be correlated with data indicating particular treatment plans for fighting or measuring infection due to different types of movements, activities, or resting position of the patient 18. For example, it may be determined that supplying enhanced electrical energy during periods of walking movement is detrimental to fighting infection. If so, then the electrical energy supplied to the percutaneous implants 12 during periods of walking movement may be reduced or eliminated.

The power source 50, the electrical sensor 52, the non-transitory computer readable medium 62, the modem 64, and the position system 68 may be coupled to the processor 58 with a bus, for example. In one embodiment, the housing 40 supports the power source 50, the electrical sensor 52, the processor 58, the non-transitory computer readable medium 62, the modems 64a-n, and the position system 68. The power source 50 can be attached to the leads 38a-e via hardware ports supplied on an exterior of the housing 40. The electrical device 30 may also be provided with a power supply 70.

The power supply 70 may be any source configured to supply electrical energy to components of the electrical device 30. For example, in some non-limiting embodiments, the power supply 70 may be a replaceable/disposable battery, a rechargeable battery such as a 5V battery, and/or a solar cell.

The processor 58 may include a single processor or multiple processors working independently and/or together to execute the logic described herein. In some non-limiting embodiments, the processor 58 may include two processors that may or may not be located in a single physical location. In some non-limiting embodiments, the processor 58 may be partially or completely network-based and/or cloud-based. As used herein, the terms "network-based," "cloud-based,"

and any variations thereof, may include the provision of configurable computational resources on demand via interfacing with a computer and/or computer network, with software and/or data at least partially located on the computer and/or computer network, and/or by pooling processing power of two or more networked processors.

The non-transitory computer readable medium 62 (shown in FIG. 2 as non-transitory memory) may be implemented as a conventional non-transitory memory, such as (but not limited to) random access memory (RAM), read only memory (ROM), flash memory, combinations thereof, and/or the like, for example. The term non-transitory computer readable medium, as used herein, may be implemented as a single physical device or multiple physical devices of a distributed system that may or may not be logically related. To that end, the non-transitory computer readable medium 62 may be located in the same physical location. Alternatively, the non-transitory computer readable medium 62 may be located in a different location and communicate via a network. Additionally, the non-transitory computer readable medium 62 may be implemented as a "cloud memory" (i.e., one or more memories may be partially or completely based on or accessed using a network, for example).

The non-transitory computer readable medium 62 may store processor executable code and/or information comprising one or more databases and program logic. In some non-limiting embodiments, the processor executable code may be stored as a data structure, such as (but not limited to) a database and/or data table, for example. In some non-limiting embodiments, data captured by the electrical sensor(s) 52 may be time-stamped and stored in the database and analysed to determine trends and/or changes in the data over time to determine whether or not any of the tissue surrounding the percutaneous implants 12 is infected. In these embodiments, a signal received from the electrical sensor(s) 52 may be compared to a stored infection parameter to determine at least one of the presence or change of infection of the tissue of the patient 18. The stored infection parameter can be data obtained from electrical sensor(s) at an earlier time period. In some non-limiting embodiments, the stored infection parameter may be determined from multiple signals received from the electrical sensor(s) 52 at the earlier time periods. For example, the stored infection parameter may be a median or average of values obtained at the earlier time periods. In other embodiments, the database(s) and program logic may include an artificial intelligence network trained with a percutaneous implant data model to determine at least one of the presence or change of infection of the tissue. The percutaneous implant data model may be trained with data in which electrical signals are received and the presence or absence of an infection is tested by methodologies not involving the electrical device 30. The logic can direct the power source 50 to apply the electrical energy continuously or intermittently. The power source 50 can be configured to apply electrical energy to multiple percutaneous implants 12. The terms first power source, second power source, etc. may refer to the same power source 50, which in this embodiment uses common components to provide the functionality of multiple power sources. In some non-limiting embodiments, the power sources 50 are separate and use separate components. The electrical energy can be applied to all of the percutaneous implants 12 at the same time, or alternately between different percutaneous implants 12 at different times. This can be based on the infection status of each percutaneous implant 12 individually.

In one embodiment, the electrical device 30 is first used as a sensor to measure the conductivity of each percutaneous implant 12 immediately after the initial surgical placement. The measured conductivity information can be stored in the non-transitory computer readable medium 62 and used as a baseline for subsequent measurements. The electrical device 30 then can be used to monitor the conductivity within the circuit for each percutaneous implant 12 at regular intervals of time as a measurement of implant site infection. If the processor 58 of the electrical device 30 detects a change in implant site conductivity during a time period after surgery (e.g., days, weeks or months after surgery), the processor 58 can automatically apply electrical energy to the particular percutaneous implant 12 to treat the detected infection. The level of treatment voltage can be varied depending on the measured change in implant site conductivity.

Logic may be embodied in the form of software instructions and/or firmware and may be executed on appropriate hardware. For example, logic embodied in the form of software instructions or firmware may be executed via the processor 58. In some non-limiting embodiments, the logic may be implemented in a stand-alone environment or in a networked environment.

Figure 2A:
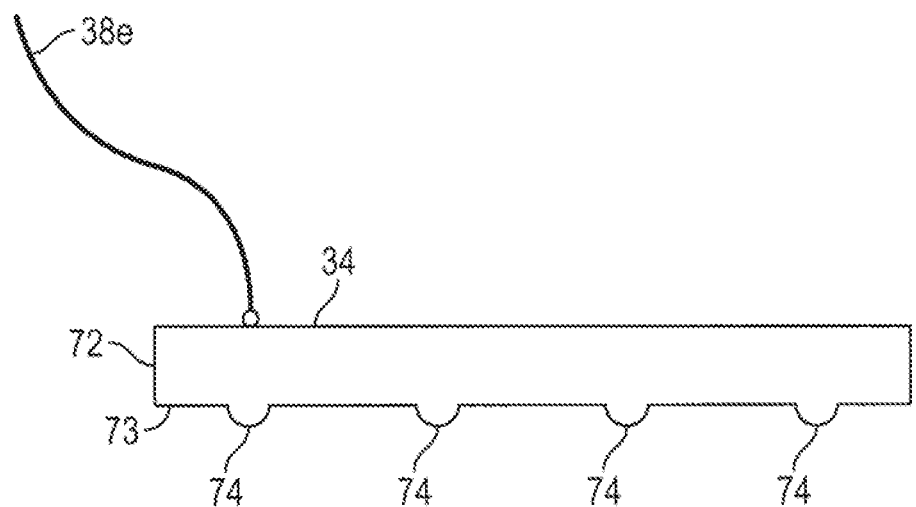
FIG. 2A is a side elevational view of an exemplary reference electrode constructed in accordance with the present disclosure.
Figure 2B:
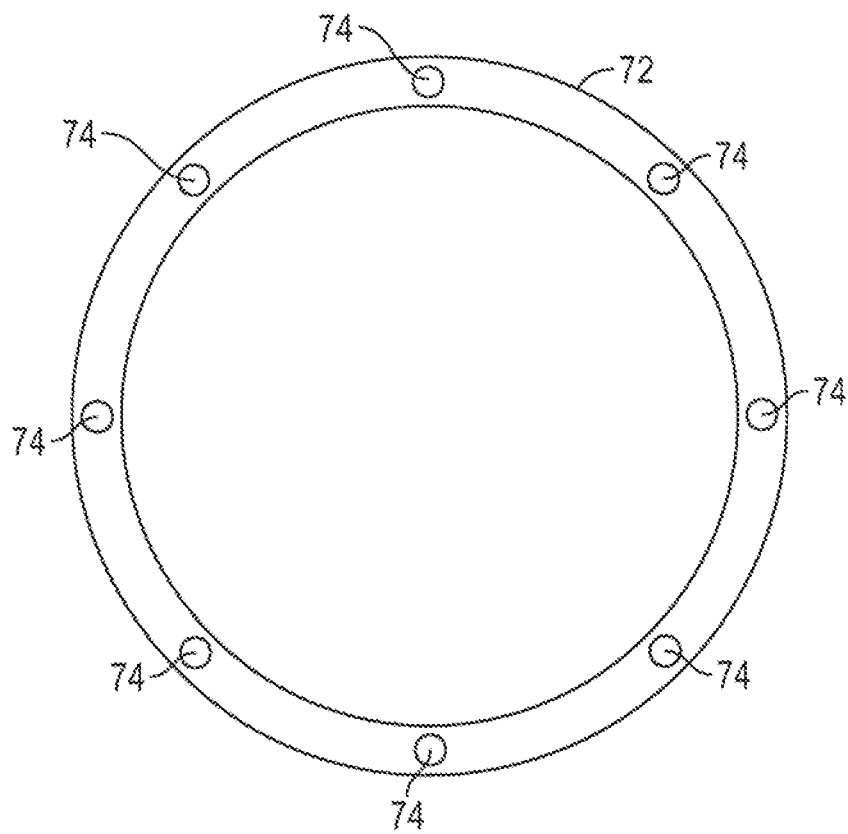
FIG. 2B is a bottom plan view of the exemplary reference electrode of FIG. 2A.

Shown in FIGS. 2A and 2B is one embodiment of the reference electrode 34 constructed in accordance with the present disclosure. In this embodiment, the reference electrode 34 includes a ring conductor 72 having a bottom surface 73 and a plurality of spatially disposed conductive protrusions 74 extending from the bottom surface 73 of the ring conductor 72. In use, the reference electrode 34 is placed on the skin 20 of the patient 18 such that the conductive protrusions 74 engage the skin 20 of the patient 18.

Figure 3:
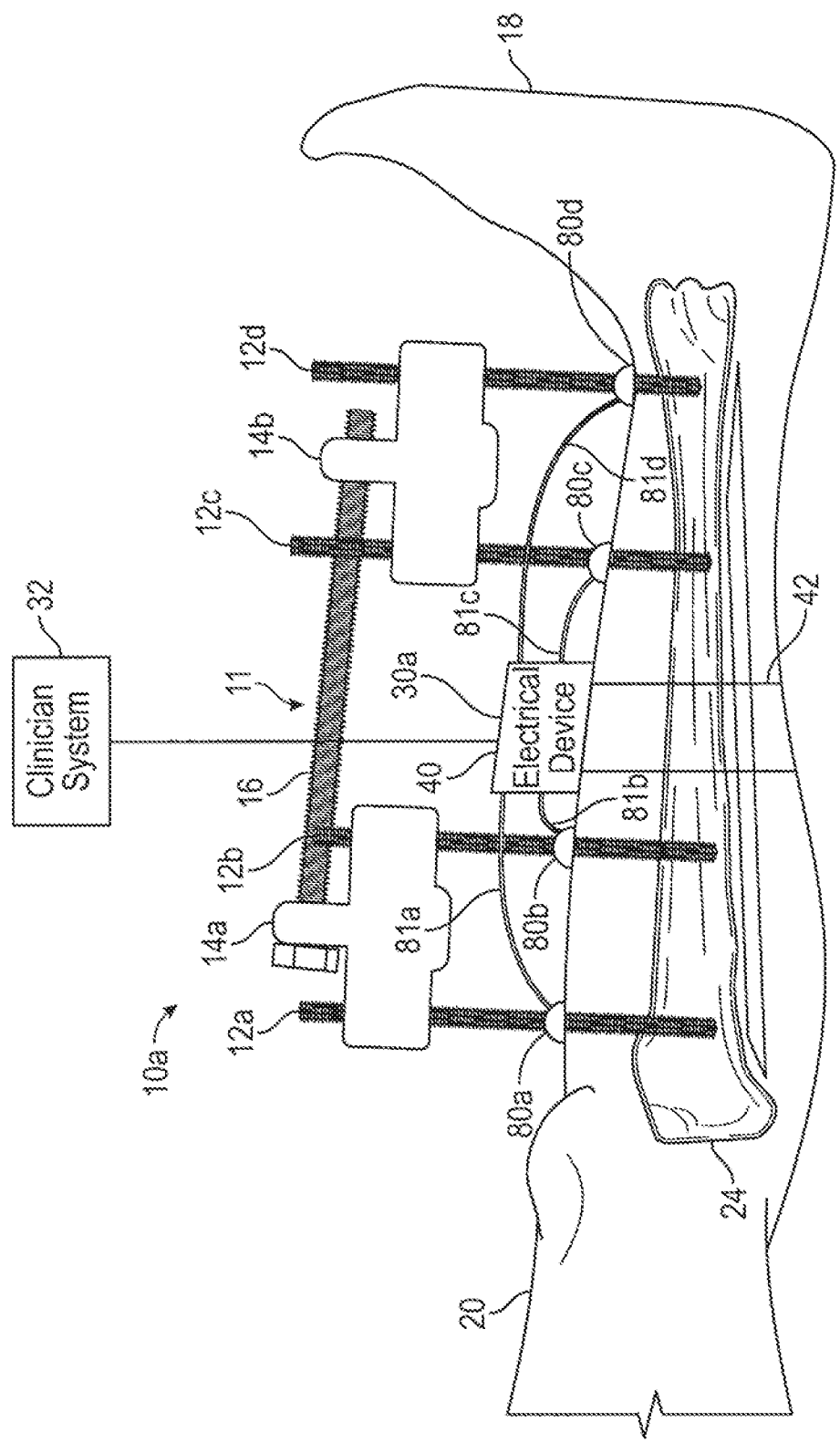
FIG. 3 is a diagrammatic view of another embodiment of an external fixation system including an electrical device constructed in accordance with the present disclosure.
Figure 4:
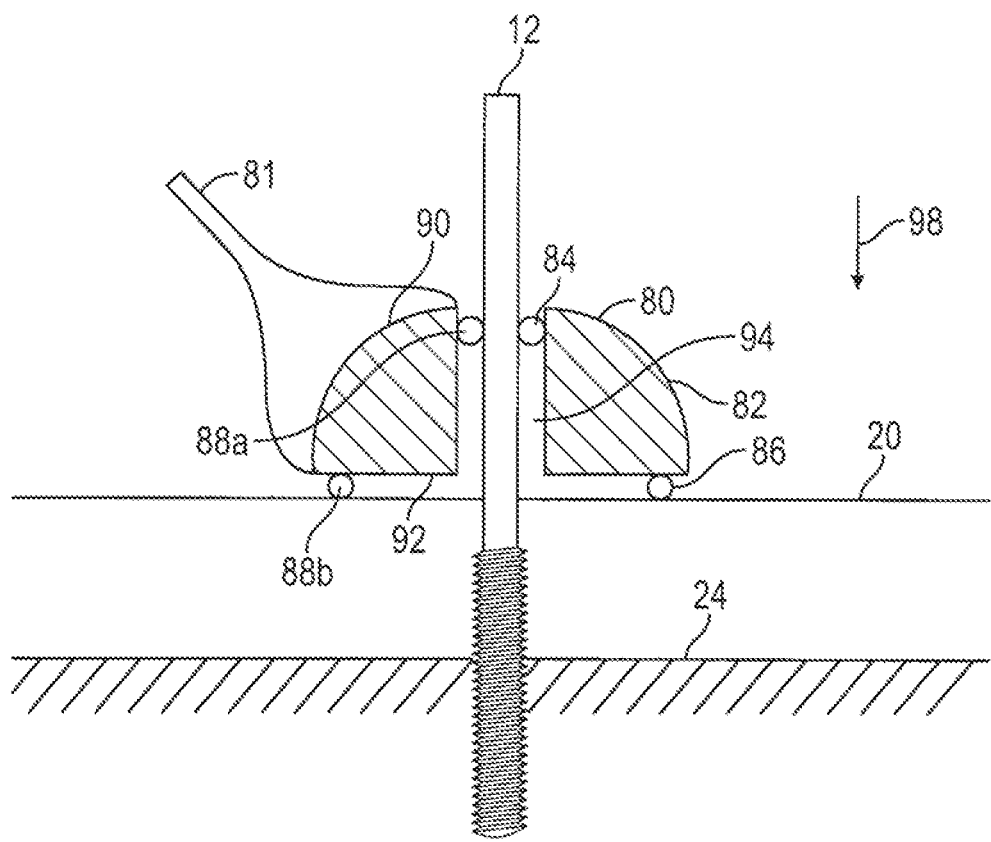
FIG. 4 is a side elevational view of an implant connector constructed in accordance with the present disclosure.

Shown in FIGS. 3 and 4 is another embodiment of an external fixation system 10a constructed in accordance with the present disclosure. The external fixation system 10a is similar in construction and function to the external fixation system 10 described above, with the exception that the processor 58 of the electrical device 30a is programmed to monitor a separate reference electrode associated with each percutaneous implant 12. This assists the system 10a in electrically isolating each of the circuits formed with one of the percutaneous implants 12. The at least one electrical parameter (e.g., conductivity or resistance) can then be determined independently for the circuit including each percutaneous implant 12 and then used to determine the infection status for the percutaneous implant 12. The external fixation system 10a is provided with a plurality of implant connectors 80 constructed in accordance with the present disclosure. Four implant connectors 80 are illustrated in FIG. 3 by way of example, and designated with the reference numerals 80a-d. Each implant connector 80a-d is connected to one of the percutaneous implants 12. The implant connectors 80 are connected to the power source(s) 50 of the electrical device 30a with leads 81a-d. The leads 81a-d may each have at least two conductors so as to supply power and ground to the implant connectors 80.

FIG. 4 shows a cross-sectional diagram of the implant connector 80. As shown in FIG. 4, the implant connector 80 is sized and dimensioned to be connected to one of the percutaneous implants 12. The implant connector 80 includes a body 82, a first electrode 84, and a second electrode 86. The body 82, the first electrode 84 and the second electrode 86 are designed such that the implant connector 80 can be separated into at least two connectable components to allow the implant connector 80 to be placed on one of the percutaneous implants 12. The body 82 supports the first electrode 84 and the second electrode 86. The first electrode 84 is positioned to engage the percutaneous implant 12, and the second electrode 86 is positioned to engage the skin 20 of the patient 18. The first electrode 84 is electrically isolated from the second electrode 86. For example, the body 82 can be constructed of a non-conductive material, such as plastic, that electrically isolates the first electrode 84 from the second electrode 86. In other embodiments, the body 82 can be at least partially constructed of an electrically conductive material, such as aluminum, steel or copper, so long as the first electrode 84 is electrically isolated from the second electrode 86. In the example shown, the first electrode 84 is provided with a ring shape, and the second electrode 86 is provided with a ring shape, although other shapes of the first electrode 84 and/or the second electrode 86 can be used. For example, the first electrode 84 can be in the form of a spring metal contact that presses against the percutaneous implant 12 from two or more directions, for example. A first conductor 88a of the lead 81 is connected to the first electrode 84, and a second conductor 88b of the lead 81 is connected to the second electrode 86.

More particularly, the body 82 is provided with an upper end 90, a lower end 92, and an opening 94 extending from the upper end 90 to the lower end 92. The opening 94 is sized and dimensioned to matingly receive the percutaneous implant 12 when installing the implant connector 80 on the percutaneous implant 12. The first electrode 84 borders the opening 94 and is positioned to engage the percutaneous implant 12 and form an electrical connection upon the implant connector 80 being positioned on the percutaneous implant 12. The second electrode 86 may be connected to the body 82 and positioned on the lower end 92 so as to extend from the lower end 92. In some embodiments, the implant connector 80 is constructed to allow lateral access to the opening 94. For example, the implant connector 80 may be constructed of two components that can be attached around the percutaneous implant 12 from the side, and then slid on the percutaneous implant 12 toward the skin 20. For example, the implant connector 80 can be provided with a hinge to allow a portion of the implant connector 80 to be moved and form an access pathway to the opening 94. Or, the implant connector 80 can be constructed of two components that can be separated, and then snapped or otherwise connected together on the percutaneous implant 12.

The implant connector 80 can be applied after the adjustable fixator 11 is connected to the percutaneous implants 12. To install each of the implant connectors 80 on one of the percutaneous implants 12, the implant connector 80 is manipulated to form the access pathway to the opening 94 and then applied onto the percutaneous implant 12. Then, the separated components of the implant connector 80 are connected such that the percutaneous implant 12 is positioned within the opening 94, and the implant connector 80 is slid in a downwardly direction 98 toward the patient 18 until the second electrode 86 engages the skin 20 of the patient. 18. The implant connector 80 can be maintained in this position with any suitable mechanism, such as (but not limited to) a set screw extending through the body 82 and engaging the percutaneous implant 12.

Figure 4A:
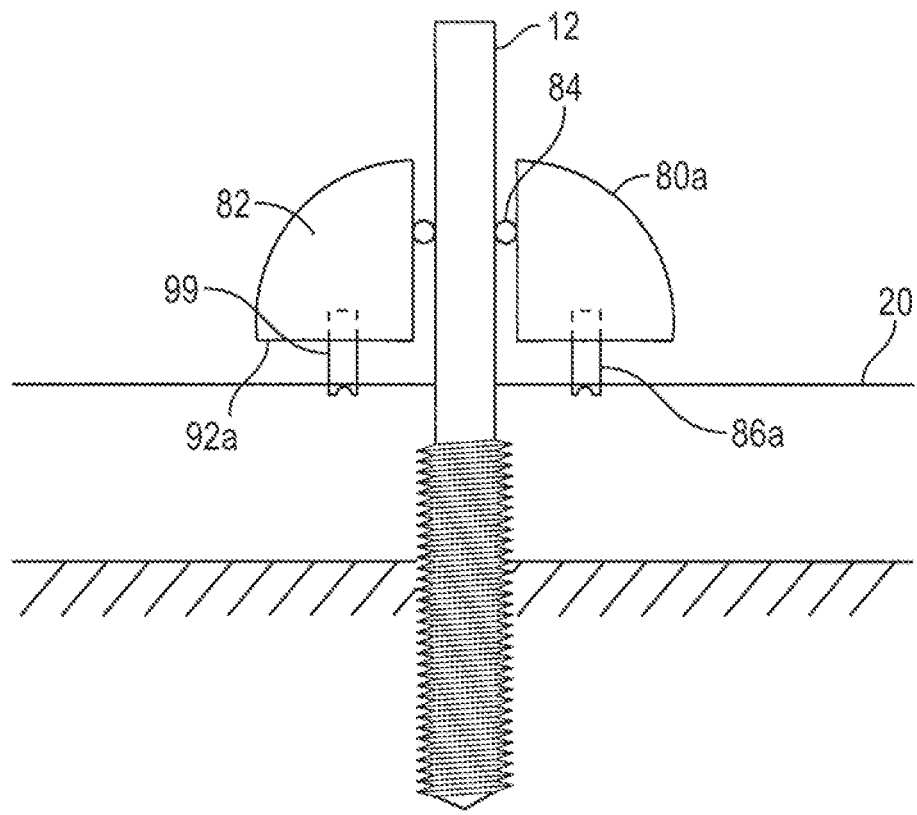
FIG. 4A is a cross-sectional view of another version of an implant connector constructed in accordance with the present disclosure.
Figure 4B:
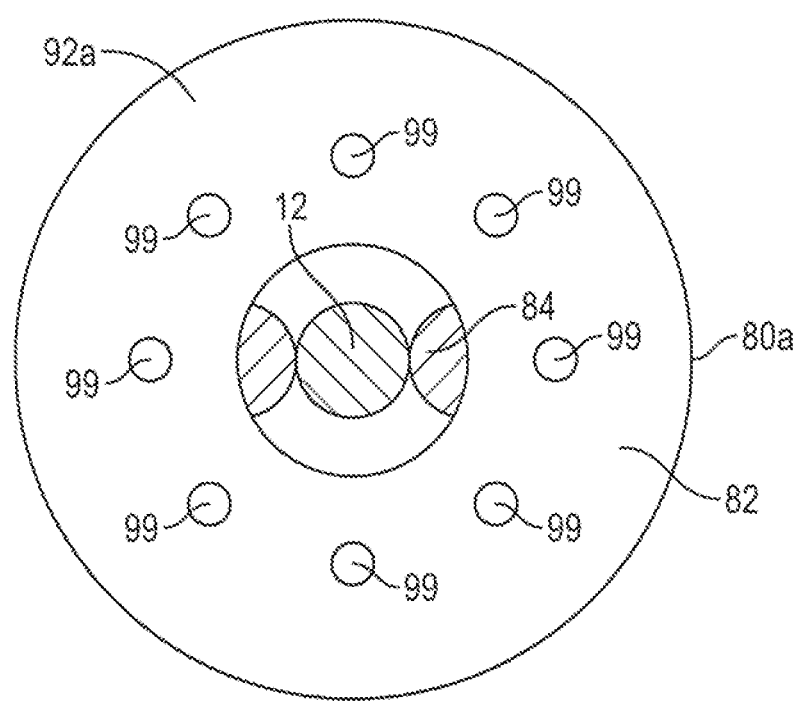
FIG. 4B is a bottom plan view of the implant connector of FIG. 4A.

Shown in FIGS. 4A and 4B and designated by the reference numeral 80a is another embodiment of an implant connector constructed in accordance with the present disclosure. The implant connector 80a is similar in construction and function as the implant connector 80, with the exception that the implant connector 80a has a second electrode 86a including multiple contacts 99 that are all electrically connected within a body 82, and protrude from a lower end 92a of the body 82a at multiple points to contact the skin 20 of the patient 18.

Figure 5:
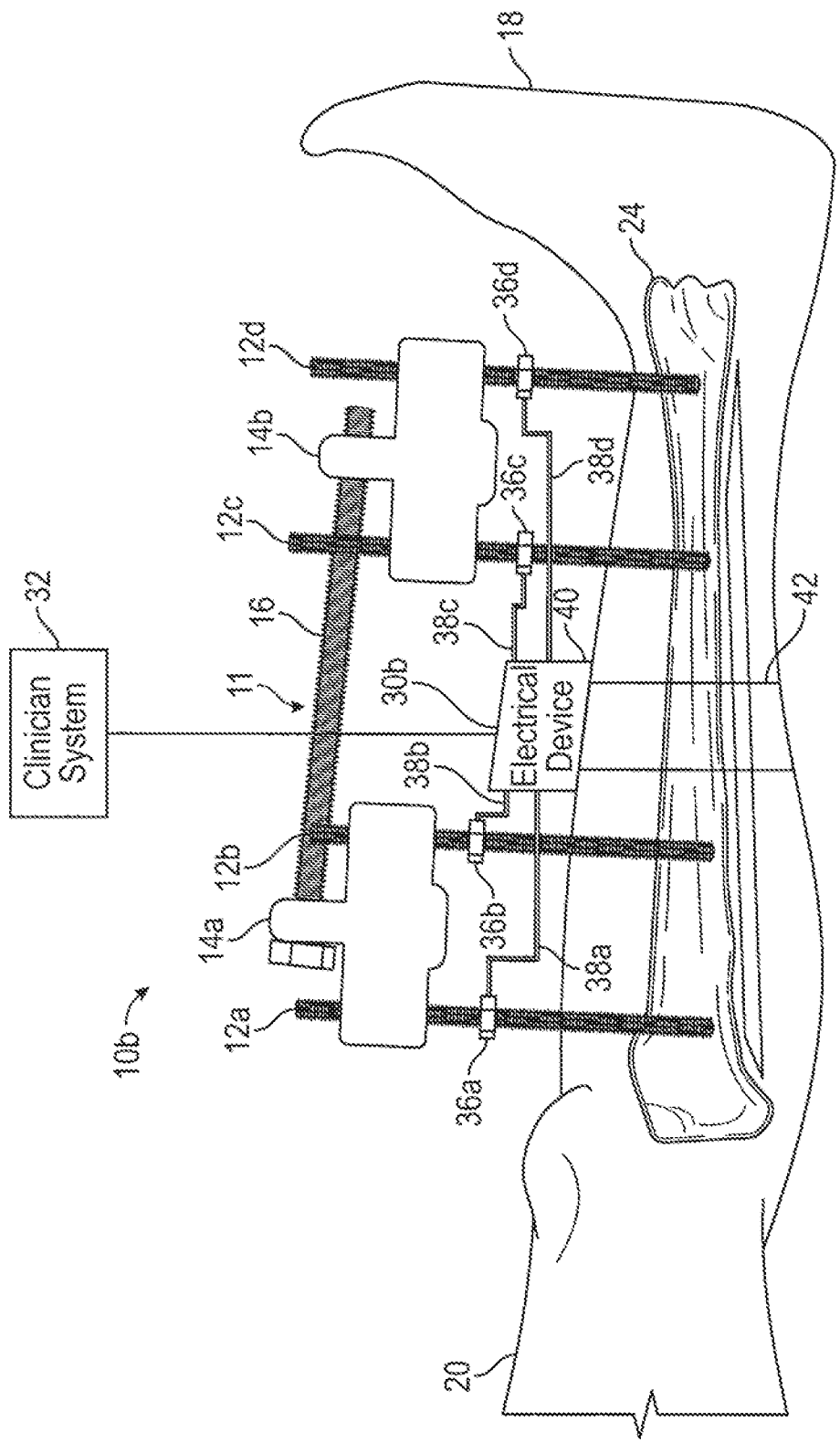
FIG. 5 is a diagrammatic view of yet another embodiment of an external fixation system having an electrical device constructed in accordance with the present disclosure.

Shown in FIG. 5 is another embodiment of an external fixation system 10b constructed in accordance with the present disclosure. The external fixation system 10b is similar in construction and function to the external fixation system 10 described above, with the exception that the processor 58 of an electrical device 30b is programmed to determine an infection status for each of the percutaneous implants 12a-d without using any electrode connected to the skin 20 of the patient 18. The processor 58 of the electrical device 30b accomplishes this by using one of the percutaneous implants 12 as a first electrode of an electrical circuit and another percutaneous implant 12 as a second electrode of the electrical circuit. The processor 58 can also be configured to use a third percutaneous implant 12 as a third electrode (e.g., reference electrode) of the electrical circuit to regulate the voltage applied between the first electrode and the second electrode. The processor 58 can send instructions to one or more of the power sources 50 to internally switch which percutaneous implant 12 is used as a positive electrode, a negative electrode, and a reference electrode, without needing to change any physical connections between the power source(s) 50 and the percutaneous implants 12. In this regard, the power source 50 may be a potentiostatic device. The potentiostatic device may be a potentiostat, a computer-controlled instrument, or any other instrument capable of maintaining a substantially constant potential or constant current flow of a first electrode relative to a second electrode.

The processor 58 may also be programmed to send instructions to one or more of the power source(s) 50 to vary the electrical potential applied to, and measure the current flow (with the electrical sensor 52) between, any two percutaneous implants 12 in the external fixation system 10b without the need for a skin electrode. This could allow the electrical device 30b to track the tissue conductivity around each of the percutaneous implants 12 independently and to treat each percutaneous implant 12 independently and automatically in response to a condition (e.g., infection status) of the tissue.

As shown in FIG. 5, the external fixation system 10b includes the plurality of implant connectors 36a-d connected to the percutaneous implants 12a-d. The electrical device 30b is also provided with the plurality of leads 38 (labelled in FIG. 5 as 38a-d) so as to connect circuitry of the electrical device 30b with the implant connectors 36a-d for supplying electrical energy to the percutaneous implants 12 and/or for monitoring the at least one electrical parameter.

Figure 6:
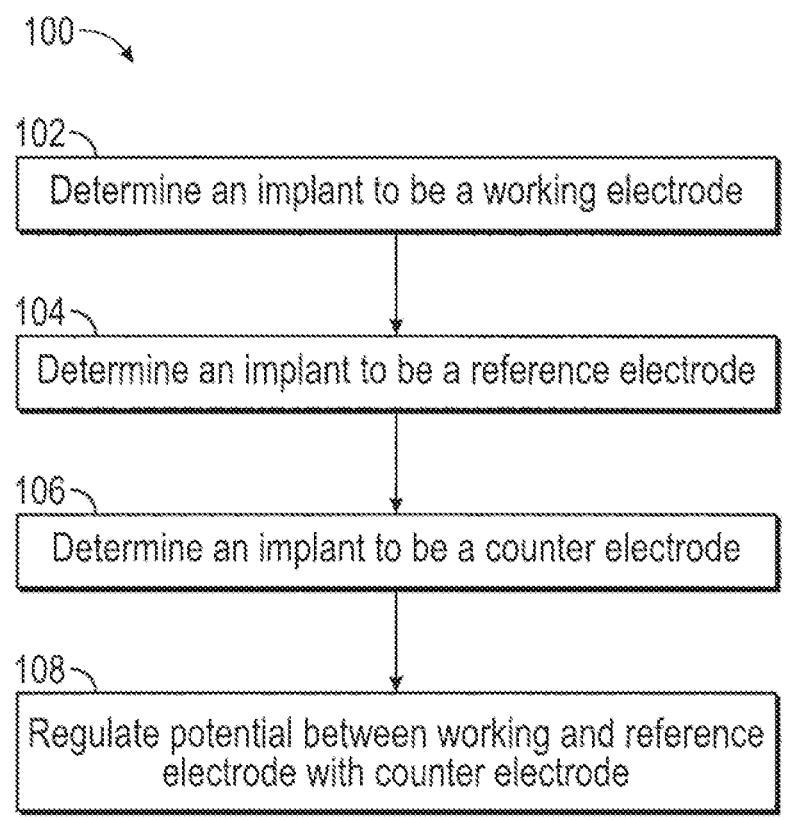
FIG. 6 illustrates a flow chart of an exemplary method for using an exemplary electrical device to reduce or eliminate an infection in accordance with the present disclosure.

FIG. 6 shows a process 100 running on the processor 58 of the electrical device 30b in accordance with the present disclosure. In the process 100, the processor 58 receives information correlating a first lead 38a of the power source 50 to a first percutaneous implant 12a, a second lead 38b of the power source 50 to a second percutaneous implant 12b, a third lead 38c of the power source 50 to a third percutaneous implant 12c, and a fourth lead 38d of the power source 50 to a fourth percutaneous implant 12d. A first circuit including the first lead 38a, for example, and the first percutaneous implant 12 is monitored for at least one electrical parameter indicative of an infection present adjacent to the first percutaneous implant 12.

In the process 100, the processor 58 cycles through steps 102, 104, and 106 to select a first set of working, reference, and counter electrodes. This can be accomplished subsequently to determining an infection status of the tissue surrounding at least one of the percutaneous implants 12a-d. In the steps 102, 104, and 106, the processor 58 determines one of the percutaneous implants 12a-d to be a working electrode; one of the percutaneous implants 12a-d to be a reference electrode; and one of the percutaneous implants 12a-d to be a counter electrode. The steps 102, 104, and 106 may be performed in an order other than the order shown in FIG. 6. Then, the processor 58 branches to a step 108 where the processor 58 regulates a potential between the working and reference electrodes with the counter electrode. Thereafter, the processor 58 can monitor the infection status of the tissue surrounding each of the percutaneous implants 12 and select another set of working, reference, and counter electrodes.

Figure 7:
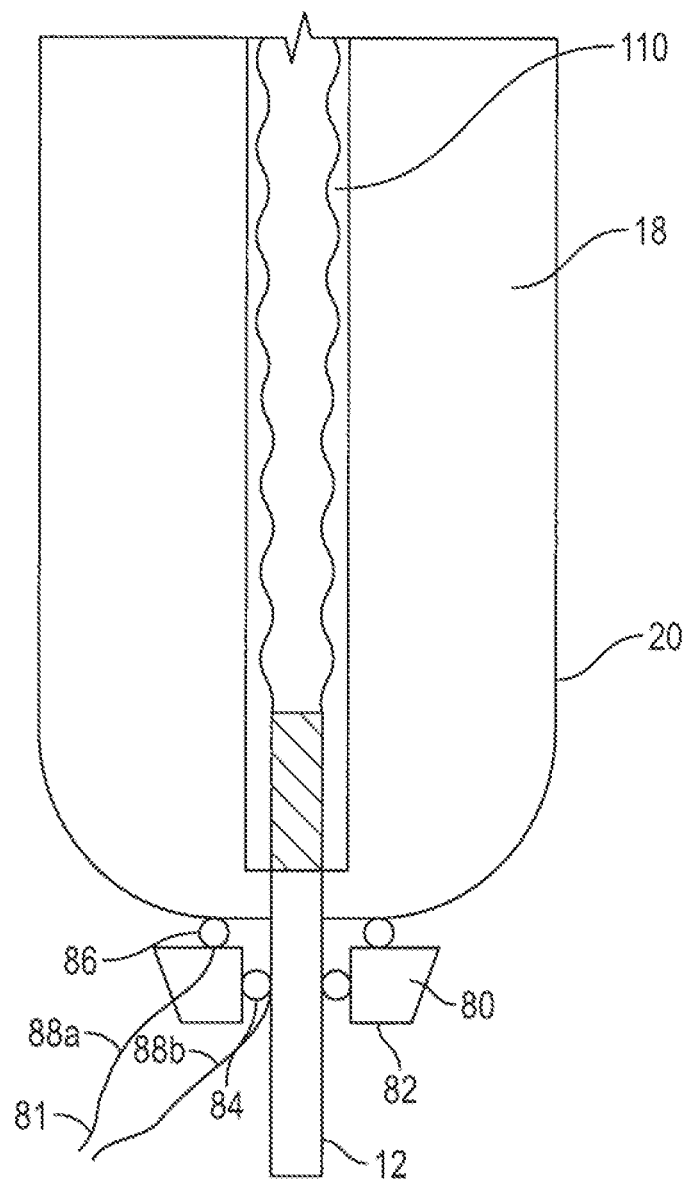
FIG. 7 is a diagrammatic view of an implant connector positioned to supply current in a circuit including a percutaneous osseointegrated prosthesis positioned within the patient's femur and extending outwardly therefrom and beyond an outer surface of the patient's skin in accordance with the present disclosure.

As discussed above, the percutaneous implant 12 can also be, in one particular but non-limiting embodiment, a percutaneous osseointegrated prosthesis. An example of the percutaneous implant 12 being a percutaneous osseointegrated prosthesis is shown in FIG. 7. In this example, the patient 18 has had a transfemoral amputation in which a lower limb of the patient 18 has been removed. The percutaneous osseointegrated prosthesis is positioned within the patient's femur 110 and extends outwardly therefrom and beyond an outer surface of the patient's skin 20. The implant connector 80 (or the implant connector 80a) is applied to the percutaneous osseointegrated prosthesis such that the first electrode 84 engages the percutaneous osseointegrated prosthesis, and the second electrode 86 engages the skin 20. Electrical current can be supplied to the first and/or the second electrode 86 via leads 81.

Described herein is a mechanism for providing a negative effect to bacteria with the use of electricity. The negative effect can be reducing the bacteria's ability to colonize the surface of the percutaneous implants 12 and thereby inhibiting or lessening the formation of a biofilm that generally increases the bacteria's susceptibility to system antibiotics or killing bacteria. The electrical devices 30, 30a, and 30b achieve this negative effect by supplying, for example but not by way of limitation, an induced electrochemical effect at the surface of the percutaneous implants 12a-d in contact with tissue. Electrical current flow causes chemical changes at the surface of the percutaneous implants 12a-d in contact with tissue, such as (but not limited to) pH or generation of reactive oxygen species. These chemical changes result in killing the bacteria present within the tissue and/or on the surface of the percutaneous implants 12a-d. These local electrochemical effects may also cause bacteria to become more sensitive to killing by local or systemic antibiotics, so that the electrical device 30, 30a, or 30b may work synergistically to enhance the effectiveness of antibiotics. The electrical energy supplied by the electrical devices 30, 30a, or 30b may be designed such that the electrical energy kills the bacteria without negatively affecting the tissue surrounding the percutaneous implants 12a-d. In one embodiment, the electrical devices 30, 30a, and 30b are applied to percutaneous external fixation implants 12 following placement of an external fixation construct. The electrical devices 30, 30a, and 30b may be configured to measure the electrical conductivity of the local tissue adjacent to the percutaneous implants 12, and to compare the conductivity values to reference values. If the electrical devices 30, and 30a detect a difference in skin conductivity indicative of a local infection, the electrical devices 30, and 30a, may apply a voltage between the percutaneous implant 12 and the reference electrode 34 or the second electrode 86 adjacent to the percutaneous implant 12. The voltage can be controlled to cause a constant electrical current to pass through the skin 20 from the percutaneous implant 12 to the reference electrode 34 or the second electrode 86. The electrical devices 30, 30a, and 30b continue to monitor the tissue conductivity, and can adjust the applied electrical current based on changes on conductivity. The applied current may be applied continuously at a specific voltage or a specified current. The current may also be applied intermittently, with periods of electrical potential alternating with periods of no potential applied. For example, an electrical potential may be applied for 10 minutes, followed by 50 minutes of no applied voltage, and this pattern repeated every hour. In another example, the electrical potential may be applied for one minute, followed by a period of no applied potential for 4 minutes, then this pattern repeated. In another example, electrical potential may be applied for 8 hours, followed by 16 hours with no applied potential, and this pattern repeated once per day. Alternately, a higher "treatment" potential may be applied for a period of time, alternated with a lower "monitoring" potential for a period of time. For example, an electrical potential sufficient to kill bacteria may be applied for 10 minutes, then a lower potential sufficient to measure the local tissue conductivity may be applied for 50 minutes, and the pattern repeated every hour. In another example, an electrical potential sufficient to kill bacteria may be applied for 10 minutes, then a lower potential sufficient to measure the local tissue conductivity may be applied for 1 minute, followed by a period of 49 minutes with no potential applied, and the pattern repeated every hour. The electrical devices 30, 30a, and 30b may be configured to apply a different potential to each implant 12 in the external fixation construct, or to only apply voltages to some of the implants 12 and not others as needed Further, in some embodiments, the housing 40 can be integrated with the body 82. In these embodiments, all of the electronics (e.g., the power source 50, the electrical sensor 52, the data processing system 54, processor 58, non-transitory computer readable medium 62, modem 64, position system 68 and the power supply 70 and leads) are included in the implant connector 80 or 80a, having the first electrode 84 on the percutaneous implant 12 and the second electrode 86 on the skin 20, with no other box or wires needed. In other words, the electrical device 30 or 30a can be a miniaturized, fully contained device with all power supply, electronics, and wireless capability enclosed in a single unit attached at the interface of the percutaneous implant 12 and the skin 20. This would be especially useful when the percutaneous implant 12 is the percutaneous osseointegrated prosthesis for amputees. In this embodiment, it is contemplated that the electrical device 30 or 30a may communicate with one another and adjust the amount of potential applied to the percutaneous implant 12 in a coordinated manner controlled by one or more of the data processing systems 54 alone or in combination with one or more of the other data processing systems 54.

From the above description, it is clear that the inventive concepts disclosed and claimed herein are well adapted to carry out the objects and to attain the advantages mentioned herein, as well as those inherent in the present disclosure. While exemplary embodiments of the inventive concepts have been described for purposes of this disclosure, it will be understood that numerous changes may be made which will readily suggest themselves to those skilled in the art and which are accomplished within the spirit of the inventive concepts disclosed and claimed herein.

What is claimed is:

1. A device, comprising:
a housing;
a power source configured to supply electrical power to a conductive percutaneous implant in a circuit including the conductive percutaneous implant and tissue of a patient adjacent to the conductive percutaneous implant;
an electrical sensor configured to generate a signal indicative of at least one electrical parameter of the circuit; and
at least one data processing system having one or more processors configured to receive the signal and analyze the signal to determine at least one of a presence or change of infection of the tissue, and pass a control signal to the power source to vary the electrical power responsive to determining at least one of the presence or change of infection of the tissue.

2. The device of claim 1, wherein the housing is configured to be worn by the patient.

3. The device of claim 1, wherein the electrical sensor monitors resistance within the circuit.

4. The device of claim 1, wherein the power source includes a reference electrode configured to be placed upon a skin of the patient.

5. The device of claim 1, wherein the power source is connected to an implant connector sized and dimensioned to be connected to the conductive percutaneous implant, the implant connector having a body, a first electrode, and a second electrode, the body supporting the first electrode and the second electrode, the first electrode positioned to engage the conductive percutaneous implant, and the second electrode positioned to engage a skin of the patient, the first electrode being electrically isolated from the second electrode.

6. The device of claim 1, wherein the power source includes a reference electrode configured to be within the circuit, the reference electrode having an implant connector configured to be connected to a second conductive percutaneous implant.

7. The device of claim 1, further comprising a wireless communication device, and wherein the one or more processors is configured to provide an alert to the wireless communication device and enable the wireless communication device to transmit the alert based upon the control signal.

8. The device of claim 1, wherein analyzing the signal includes supplying the signal to an artificial intelligence network trained with a percutaneous implant data model to determine at least one of the presence or change of infection of the tissue.

9. The device of claim 1, wherein analyzing the signal includes comparing the signal to a stored infection parameter to determine at least one of the presence or change of infection of the tissue.

10. The device of claim 1, wherein varying the electrical power includes increasing or decreasing an amount of the electrical power.

11. A wearable device, comprising:
a housing configured to be worn by a patient;
a first power source configured to supply first electrical power to a conductive percutaneous implant in a circuit including the conductive percutaneous implant and a tissue adjacent to the conductive percutaneous implant,
an electrical sensor configured to generate a signal indicative of at least one electrical parameter of the circuit; and
at least one data processing system having one or more processors configured to receive the signal and analyze the signal to determine an infection status of the tissue, the infection status determined to be infected, not infected, or some changed amount of infection as compared to a prior infection state baseline and pass a control signal to the power source to vary the electrical power responsive to the infection status of the tissue being infected.

12. The wearable device of claim 11, wherein the housing has a band configured to be worn by the patient.

13. The wearable device of claim 11, wherein the electrical sensor monitors resistance within the circuit.

14. The wearable device of claim 11, wherein the power source includes a reference electrode configured to be placed upon a skin of the patient.

15. The wearable device of claim 11, wherein the power source is connected to an implant connector sized and dimensioned to be connected to the conductive percutaneous implant, the implant connector having a body, a first electrode, and a second electrode, the body supporting the first electrode and the second electrode, the first electrode positioned to engage the conductive percutaneous implant, and the second electrode positioned to engage a skin of the patient, the first electrode being electrically isolated from the second electrode.

16. The wearable device of claim 11, and wherein the power source includes a reference electrode configured to be within the circuit, the reference electrode having an implant connector configured to be connected to a second conductive percutaneous implant.

17. The wearable device of claim 11, further comprising a wireless communication device, and wherein the one or more processors is configured to provide an alert to the wireless communication device and enable the wireless communication device to transmit the alert responsive to the infection status of the tissue determined to be infected.

18. The wearable device of claim 11, wherein analyzing the signal includes supplying the signal to an artificial intelligence network trained with a percutaneous implant data model to determine the infection status of the tissue.

19. The wearable device of claim 11, wherein analyzing the signal includes comparing the signal to a stored infection parameter to determine the infection status of the tissue.

20. The wearable device of claim 11, wherein varying the electrical power includes increasing an amount of the electrical power.

* * * * *